(12) United States Patent
De Kock et al.

(10) Patent No.: US 10,842,520 B2
(45) Date of Patent: Nov. 24, 2020

(54) DOTTERING TOOLS FOR IMPLANTING MEDICAL DEVICES

(71) Applicant: CARDIAC PACEMAKERS, INC., St. Paul, MN (US)

(72) Inventors: Andrew L. De Kock, Andover, MN (US); G. Shantanu Reddy, Minneapolis, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 908 days.

(21) Appl. No.: 15/284,629

(22) Filed: Oct. 4, 2016

(65) Prior Publication Data

US 2017/0100148 A1    Apr. 13, 2017

Related U.S. Application Data

(60) Provisional application No. 62/240,251, filed on Oct. 12, 2015.

(51) Int. Cl.
*A61B 17/32* (2006.01)
*A61M 25/01* (2006.01)
(Continued)

(52) U.S. Cl.
CPC ... *A61B 17/32002* (2013.01); *A61M 25/0147* (2013.01); *A61M 25/0194* (2013.01); *A61B 17/3468* (2013.01); *A61B 2017/003* (2013.01); *A61B 2017/00292* (2013.01); *A61B 2017/00398* (2013.01); *A61B 2017/00544* (2013.01);
(Continued)

(58) Field of Classification Search
CPC .......... A61B 17/32002; A61B 17/3468; A61B 2017/00292; A61B 2017/003; A61B 2017/00398; A61B 2017/00544; A61B 2017/00734; A61B 2017/00853; A61B 2017/00876; A61B 2017/320028; A61B 2017/320032; A61B 2017/320056; A61B 2017/32096; A61M 2025/0062; A61M 2025/0197; A61M 25/0052; A61M 25/0141; A61M 25/0147; A61M 25/0152;
(Continued)

(56) References Cited

U.S. PATENT DOCUMENTS 4,883,460 A    11/1989 Zanetti et al.
5,116,350 A *  5/1992 Stevens .......... A61B 17/320758
                                              606/159

(Continued)

OTHER PUBLICATIONS

International Search Report and Written Opinion, PCT/US2016/055319, dated Jan. 5, 2017.
(Continued)

*Primary Examiner* — Elizabeth Houston
*Assistant Examiner* — Socrates L Boutsikaris
(74) *Attorney, Agent, or Firm* — Seager, Tufte & Wickhem LLP

(57) ABSTRACT

Insertion tools for medical applications. An illustrative example is an insertion tool for implanting a lead such as a subcutaneous defibrillation lead, which includes a handle at a proximal end, a catheter, and a distal end. A plurality of stylets having dottering tips are provided in the insertion tool. Reciprocating action of the dottering tips and/or stylets is imparted to dissect through subcutaneous tissue and create a tunnel for implantation of the lead.

7 Claims, 13 Drawing Sheets

(51) Int. Cl.
  *A61B 17/00* (2006.01)
  *A61B 17/3209* (2006.01)
  *A61N 1/05* (2006.01)
  *A61M 25/00* (2006.01)
  *A61B 17/34* (2006.01)

(52) U.S. Cl.
  CPC ............... *A61B 2017/00734* (2013.01); *A61B 2017/00853* (2013.01); *A61B 2017/00876* (2013.01); *A61B 2017/320028* (2013.01); *A61B 2017/320032* (2013.01); *A61B 2017/320056* (2013.01); *A61B 2017/32096* (2013.01); *A61M 25/0052* (2013.01); *A61M 25/0141* (2013.01); *A61M 25/0152* (2013.01); *A61M 2025/0062* (2013.01); *A61M 2025/0197* (2013.01); *A61N 1/0504* (2013.01); *A61N 1/0563* (2013.01)

(58) Field of Classification Search
  CPC ............. A61M 25/0194; A61N 1/0504; A61N 1/0563
  See application file for complete search history.

(56) References Cited

U.S. PATENT DOCUMENTS

| | | | |
|---|---|---|---|
| 5,263,959 | A | 11/1993 | Fischell |
| 5,925,055 | A | 7/1999 | Adrian et al. |
| 6,638,277 | B2 * | 10/2003 | Schaefer ............ A61B 18/1477 606/34 |
| 7,655,014 | B2 | 2/2010 | Ko et al. |
| 9,216,284 | B2 | 12/2015 | O'Connor |
| 2004/0102804 | A1 | 5/2004 | Chin |
| 2011/0144671 | A1* | 6/2011 | Piippo Svendsen ........................ A61B 17/320758 606/159 |
| 2015/0209077 | A1* | 7/2015 | Marshall ............ A61B 17/3417 606/129 |

OTHER PUBLICATIONS

Darrat, Y. (May 11, 2018). B-PO05 -034 / B-PO05 -034—Single Incision Technique for Placement of Subcutaneous Implantable Cardioverter Defibrillators. Retrieved from http://abstractsonline.com/pp8/#!/4554/presentation/7501.

* cited by examiner

DOTTERING TOOLS FOR IMPLANTING MEDICAL DEVICES

CROSS REFERENCE TO RELATED APPLICATIONS

The present application claims the benefit of and priority to U.S. Provisional Patent Application Ser. No. 62/240,251, filed Oct. 12, 2015, and titled DOTTERING TOOLS FOR IMPLANTING MEDICAL DEVICES, the disclosure of which is incorporated herein by reference.

BACKGROUND

The S-ICD System™ from Cameron Health, Inc., and Boston Scientific Corporation presents a new opportunity in cardiac rhythm management to reduce the complications associated with transvenous defibrillator systems. The defibrillator system itself may be implanted subcutaneously without accessing the vasculature or touching the heart.

An illustration is provided in FIG. 1. The system is implanted in a patient 10 with a canister 12 in the left axilla at about the level of the cardiac apex. A lead 14 is placed subcutaneously, beneath the skin and over the ribcage of the patient, with a first portion extending along the inframammary crease to the xiphoid, and then superiorly parallel to and about 1-2 cm to the left of the sternum. A proximal sense electrode 16, shocking coil electrode 18, and distal tip sense electrode 20 are provided along the parasternal portion of the lead 14. The entire system is implanted outside of the ribcage.

The canister 12 may further include such components as would be appropriate for communication (such as RF communication, inductive telemetry or other suitable communication linkage) with an external device such as a programmer 22. For example, during an implantation procedure, once the canister 12 and lead 14 are placed, the programmer 22 may be used to activate the canister 12 and/or direct/observe diagnostic or operational tests. After implantation, the programmer 22 may be used to non-invasively determine the status and history of the implanted device. The programmer 22 in combination with the canister 12 may also allow annunciation of statistics, errors, history and potential problems to the user/medical practitioner, and may also allow for updating of programming in the canister 12.

As shown in FIG. 2, a typical implant for the S-ICD System uses three incisions 30, 32, 34, and a sterile field represented by shape 36 is used to avoid the introduction of microorganisms that can cause infection. Some physicians have also used a two-incision approach by foregoing the superior sternal incision 34.

FIG. 3 shows an illustrative insertion tool for implanting subcutaneous leads. The insertion tool 50 includes an elongated shaft 52 having a distal tip 54 with a suture hole 56 for attaching to an electrode during implantation, and a handle shown at 58. The shaft 52 may be malleable or shapeable to impart a curve for getting around the ribcage of a patient, and may include a lumen therethrough for infusing an analgesic such as lidocaine. Although the shaft 52 may be shaped by the user, it is not steerable, and relies on blunt force dissection to advance through tissue. Some proposed alternatives for these insertion tools have included the use of an ultrasonic transducer to assist with tunneling. Additional alternatives to these tunneling tools are desired.

Overview

Insertion tools having a plurality of individual tunneling elements that can be actuated individually, collectively, or as groups, may facilitate easier tunneling. In a first illustrative embodiment, a dottering tool for use in implanting a subcutaneous lead may comprise, a catheter having a proximal end and a distal end, a handle at the proximal end of the catheter, a plurality of stylets extending in the catheter, and having dottering tips thereon for tunneling through subcutaneous tissue, and an actuator coupled to the plurality of stylets to drive the stylets in reciprocating motion past the distal end of the catheter.

Additionally, or alternatively, in some embodiments according to the first illustrative embodiment, the actuator may include an electrical drive circuit.

Additionally, or alternatively, in some embodiments according to the first illustrative embodiment, the actuator may include a pneumatic driver.

Additionally, or alternatively, in some embodiments according to the first illustrative embodiment, the actuator may include a disk disposed such that one portion of the disk is in a forward position and another portion of the disk is in a rearward position, with the stylets connected to the disk, wherein motion of the actuator rotates the disk to bring different portions of the disk to the forward and rearward positions.

Additionally, or alternatively, in some embodiments according to the first illustrative embodiment, the stylets may be connected together to the disk in a distributed fashion such that the individual stylets take turns being in forward and rearward positions.

Additionally, or alternatively, in some embodiments according to the first illustrative embodiment, the actuator may include one or more linear reciprocating drivers, each of the one or more reciprocating drivers being coupled to one or more of the stylets.

Additionally, or alternatively, in some embodiments according to the first illustrative embodiment, the actuator may be contained primarily in the handle such that the stylets extend through the catheter from the proximal end to the distal end thereof.

Additionally, or alternatively, in some embodiments according to the first illustrative embodiment, the catheter may comprise an alignment element having a plurality of passageways for directing the plurality of stylets out the distal end of the catheter.

Additionally, or alternatively, in some embodiments according to the first illustrative embodiment, the catheter is a steerable catheter having one or more pull wires therein for deflecting the distal tip thereof, the pull wires being coupled to a steering controller in the handle.

Additionally, or alternatively, in some embodiments according to the first illustrative embodiment, the catheter may be flexible in lateral dimensions thereof such that a steerable sheath placed on the catheter can deflect the distal tip of the catheter.

Additionally, or alternatively, in some embodiments according to the first illustrative embodiment, one or more of the dottering tips may be sharpened.

Additionally, or alternatively, in some embodiments according to the first illustrative embodiment, one or more of the dottering tips may be rounded.

Additionally, or alternatively, in some embodiments according to the first illustrative embodiment, one or more of the dottering tips may be forked.

Additionally, or alternatively, in some embodiments according to the first illustrative embodiment, one or more of the dottering tips may be blunted.

Additionally, or alternatively, in some embodiments according to the first illustrative embodiment, the plurality of stylets may comprise about 10 to about 20 stylets.

In a second illustrative embodiment, a method of implanting a subcutaneous lead using a dottering tool to establish a tunnel for the subcutaneous lead, the dottering tool having a catheter with proximal and distal ends, a handle at the proximal end of the catheter, a plurality of stylets having dottering tips, and an actuator coupled to the plurality of stylets to drive the stylets in reciprocating motion, may comprise inserting the dottering tool through an incision into a subcutaneous space of a patient, activating reciprocating motion of the plurality of dottering tips, and forming a tunnel by advancing the dottering tool with the dottering tips activated in reciprocating motion through subcutaneous tissue of the patient, wherein the dottering tips dissect the subcutaneous tissue by their reciprocating motion as the tunnel is formed by advancement of the dottering tool.

Additionally, or alternatively, in any of the above embodiments according to the second illustrative embodiment, the method may further comprise inserting the dottering tool into a steerable sheath and using the steerable sheath to direct the dottering tool as it is advanced along a desired subcutaneous path.

Additionally, or alternatively, in any of the above embodiments according to the second illustrative embodiment, the dottering tool may comprise a steering wire coupled to a steering control at the handle of the dottering tool, such that the catheter is steerable, wherein the step of forming a tunnel by advancing the dottering tool includes using the steering control to direct the distal tip of the catheter along a desired subcutaneous path.

Additionally, or alternatively, in any of the above embodiments according to the second illustrative embodiment, step of activating reciprocating motion of the plurality of dottering tips may include enabling electrical actuation of the plurality of dottering tips.

Additionally, or alternatively, in any of the above embodiments according to the second illustrative embodiment, the step of activating reciprocating motion of the plurality of dottering tips may include enabling pneumatic actuation of the plurality of dottering tips.

This summary is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

As used herein, a dottering tool is a catheter device having a plurality of at least 2, and up to about 50, though preferably about 10 to about 20, individual tunneling stylets or wires having on them a specially designed end (a dottering tip) adapted for use in tunneling through tissue. The catheter may include plural lumens each dedicated to an individual one of the stylets, or may have one or more lumens having plural stylets therein. In one specific example, a single actuating drive system is used to actuate each of the stylets in series by (partial) rotation of a drive disk connected to several stylets. Alternatively, the stylets may be actuated individually, in small groups, or all as one. Actuating motion may be manual or machine driven as by, for example, a pneumatic system or an electric motor. The catheter may be flexible or rigid, as desired. The catheter may be steerable in some examples. Various uses, features and options for a dottering tool are described below.

Figure 4:
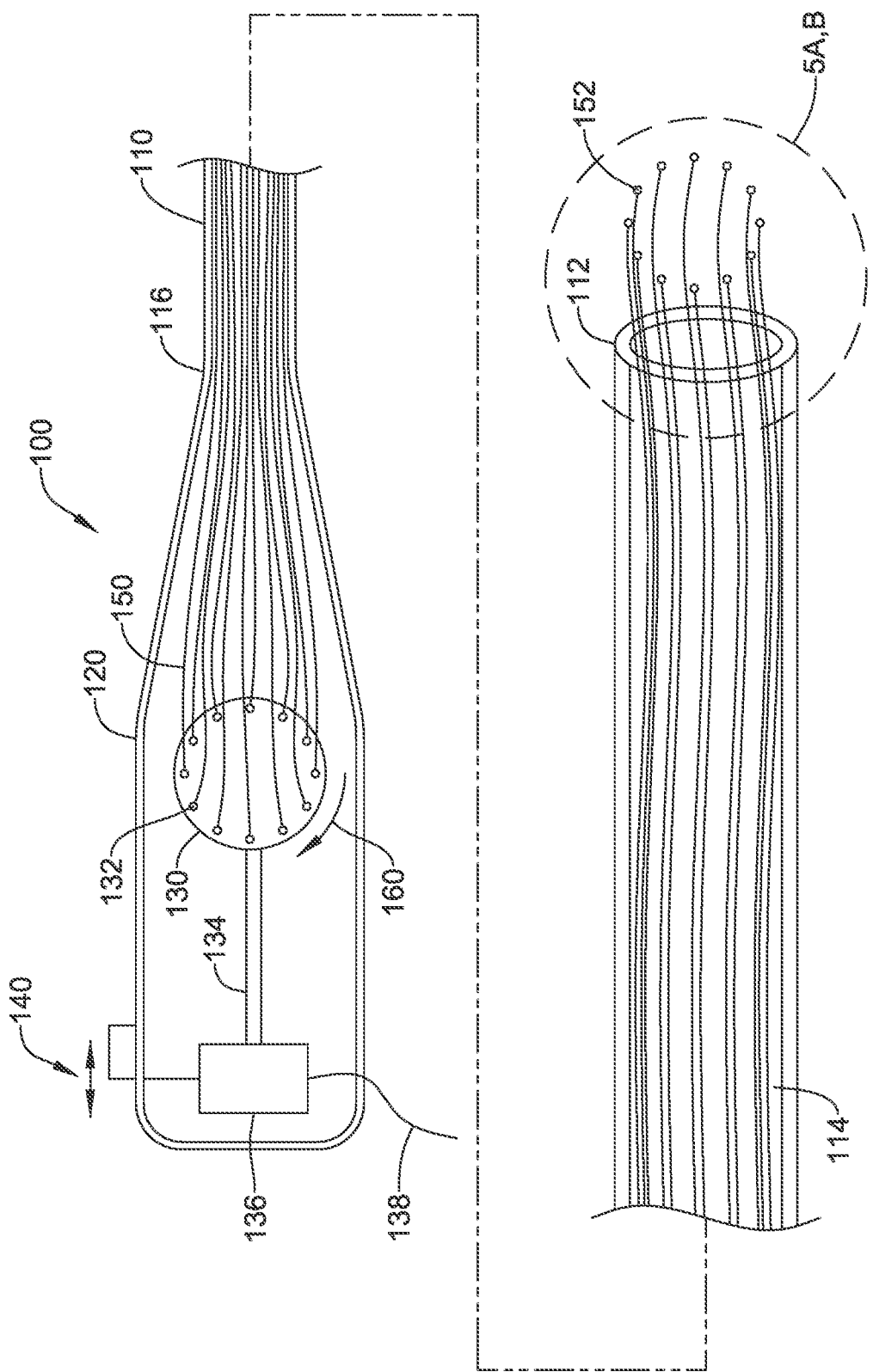
FIG. 4 shows an illustrative embodiment having a disk actuator.

FIG. 4 shows an illustrative embodiment having a disk actuator. The dottering tool 100 includes a catheter 110 and a proximal handle 120. The catheter has a distal end at 112 with stylets 114 extending therein to and proximal of the proximal end 116. The transition at the proximal end 116 of the catheter 110 to the handle 120 may be smooth or gradual or abrupt; the attachment therebetween can take many forms. Alternatively the handle 120 and catheter 110 can be a single piece.

At the distal end 112 of the catheter 110 the dottering tips 152 can be seen. The dottering tips 152 are shown at the end of stylets 114 which may be wires of stainless steel, titanium, nickel titanium (Nitinol) or other medical grade material including, for example, various biocompatible polymers. To make actuation easier by reducing friction, for example, the stylets 114 may have a lubricious coating or layer of lubricious material such as polytetrafluoroethylene (PTFE) or other materials.

The stylets 114 extend proximal of the proximal end 116 of the catheter 110 into the handle 120. An actuating disk 130 includes connections 132 to the stylets 114 adjacent proximal end regions 150 thereof. A drive shaft 134 is used to turn the drive disk back and forth as shown at 160 such that different ones of the stylets are pushed forward and back with rotation of the disk. In some examples a gear box (not shown) to convert rotation of the drive shaft 134 to the disk 130 is included.

The stylets 114 translate the motion of the disk 130 to the distal end 112 of the catheter 110, causing the dottering tips 152 to move forward and back. The connections 132 are shown distributed around the drive disk; if desired, the connections 132 may be in small clusters or all provided in a single location.

In the example of FIG. 4, an electric motor 136 is provided in the handle 120, with a switch 140 provided to turn the motor on and off. Alternatively, an external control may be provided using line 138, which may couple to a control pedal. The device may be battery powered or may have a plug for a wall outlet, for example. In other examples, shown below, pneumatic power or manual operation are discussed.

Figure 11:
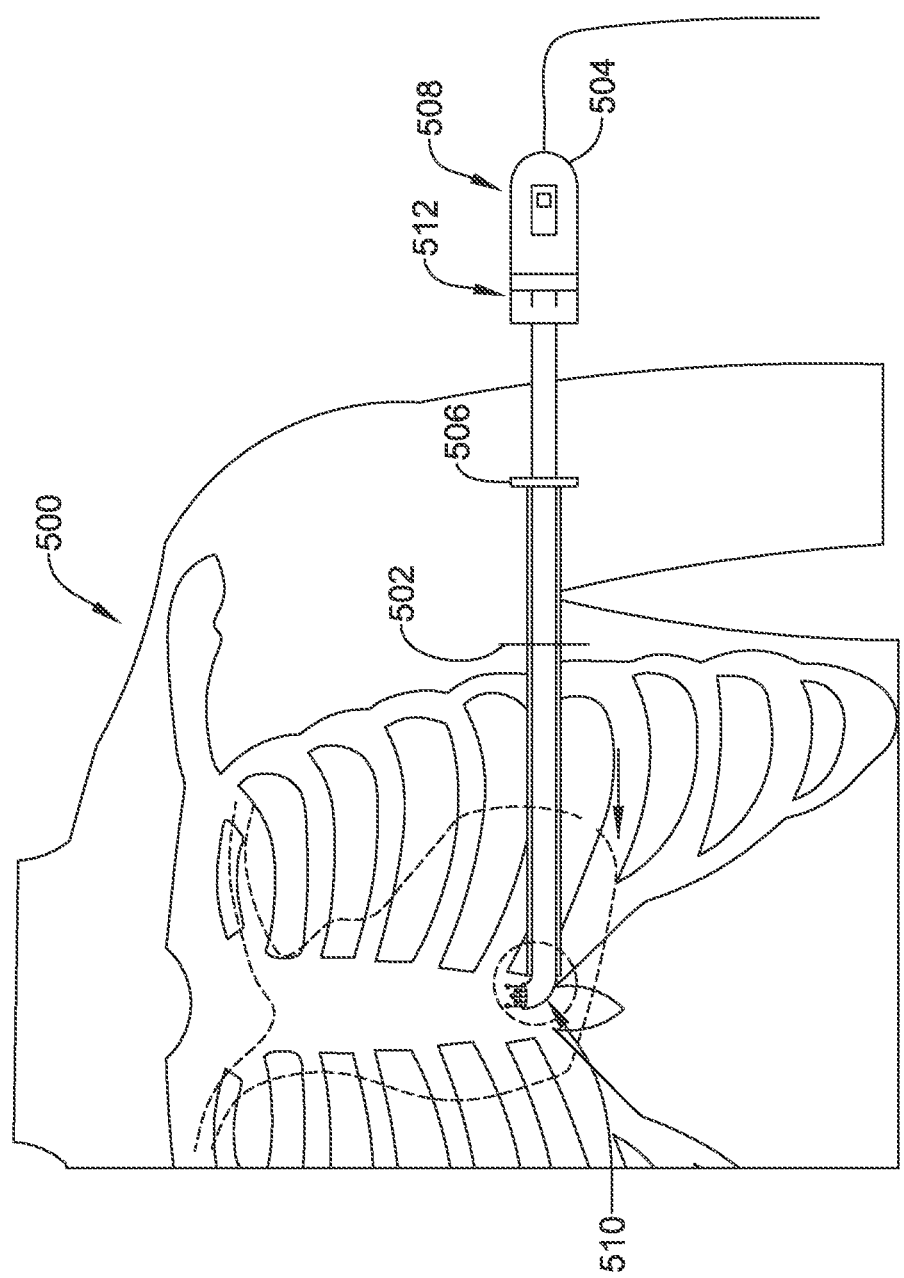
FIG. 11 shows a patient being implanted with a steerable insertion tool and sheath.

In some examples a steering mechanism, such as one or more pull wires, may extend through the catheter 110 to a region near the distal tip 112 to allow deflection thereof. FIG. 11 shows an example having external controls for steering. The catheter 110 may be any suitable medical grade material such as polyether block amide, polyurethane, silicone rubber, or other materials. The catheter 110 may include a support coil or braid, or the like to supplement column strength, robustness and/or torque capability. The catheter 110 may be a hypotube or metallic member. The catheter 110 may comprise multiple longitudinal sections connected together having varying diameters or properties such as stiffness, and or may include multiple layers of different materials.

In another example, a stowed position may be enabled in which the disk 130 can move within the handle to draw all of the stylets 114 into the catheter 110.

Figure 5B:
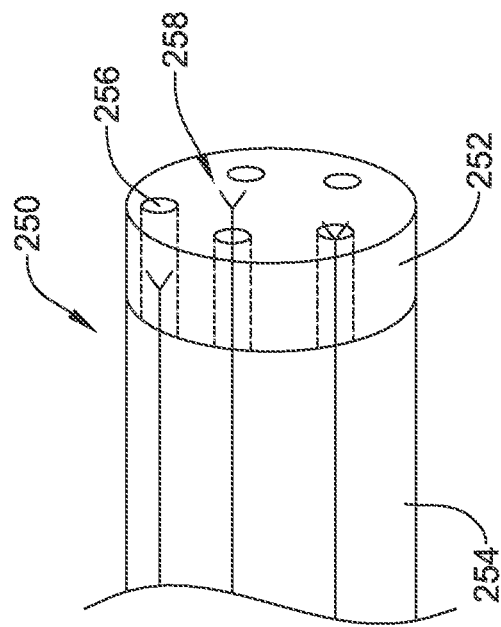
FIGS. 5A-5B show two designs for illustrative embodiments.
Figure 5A:
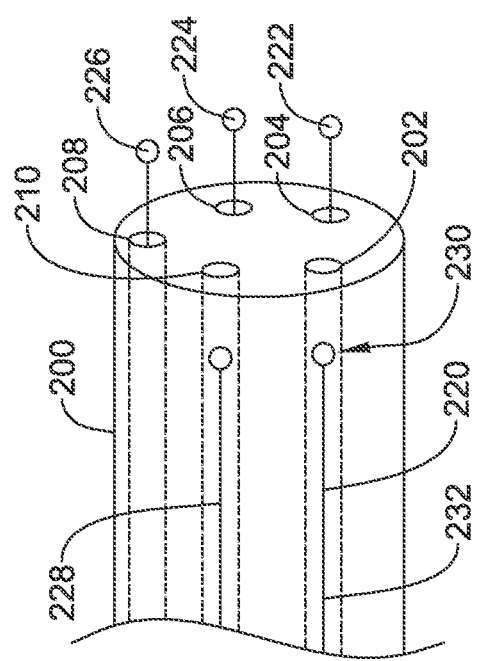

FIGS. 5A-5B show two designs for illustrative embodiments. In FIG. 5A, the catheter 200 includes a number of lumens 202, 204, 206, 208, 210, each having therein a dissector or dottering element 220, 222, 224, 226, 228. Dottering element 220 is shown as including a dottering tip 230 on the distal tip of a stylet 232. The other dottering elements 222, 224, 226, 228 are each shown with a similar design.

In the example, dottering element 224 is shown as extended out of the distal end of the catheter 200 to the greatest extent, while dottering element 228 is withdrawn into the catheter 200 to the greatest extent of all of the dottering elements 220, 222, 224, 226, 228. If connected, for example, to disk 130 of FIG. 4, as the disk 130 turns, different ones of the dottering elements will extend out of and then withdraw back into the catheter 200 in reciprocating fashion. The configuration shown would allow the most-extended dottering element 224 to move around in circular fashion such that dottering element 224 goes out, followed by 226, then 228, 220 and 222, and so forth. Those skilled in the art will recognize that an alternating sequence can be provided depending on how the various stylets are driven. For example, connecting the proximal end of the stylets to a disk 130 (FIG. 4) can be done such that the order of extension goes 224-228-222-226-220, if desired.

It may be noted that only five dottering elements 220, 222, 224, 226, 228 are shown in FIG. 5A for simplicity of illustration. In other examples a single dottering element is provided, while in still further examples, up to 50, or more, dottering elements can be provided. It is envisioned that 10 to 20 dottering elements would be used in some applications.

While FIG. 5A shows lumens running through the catheter 200, in another example, shown in FIG. 5B at 250, an insert shown as item 252 is provided within a catheter 254 having a single lumen. Item 252 defines several short lumens 256 that direct the dottering elements 258 out of the distal end of the device 250 in a desired arrangement, spacing, and/or direction.

In an alternative, item 252 is not an insert but is instead a separate catheter section attached to catheter 254 using known methods for coupling two catheter sections together such as welding, melting, inclusion of support members, and/or the use of heat shrink outer sheaths for example. Item 252 is shown at the distal end of the device 250; in another example, item 252 may be used at the proximal end of the device to connect catheter 254 to the handle. In yet another example, item 252 is an arranging disk and more than one are provided, for example, at proximal and distal ends (and possibly in the middle) of a device to avoid tangling and reduce friction between the stylets of plural dottering elements. In still another example, item 252 may be omitted.

Figure 1:
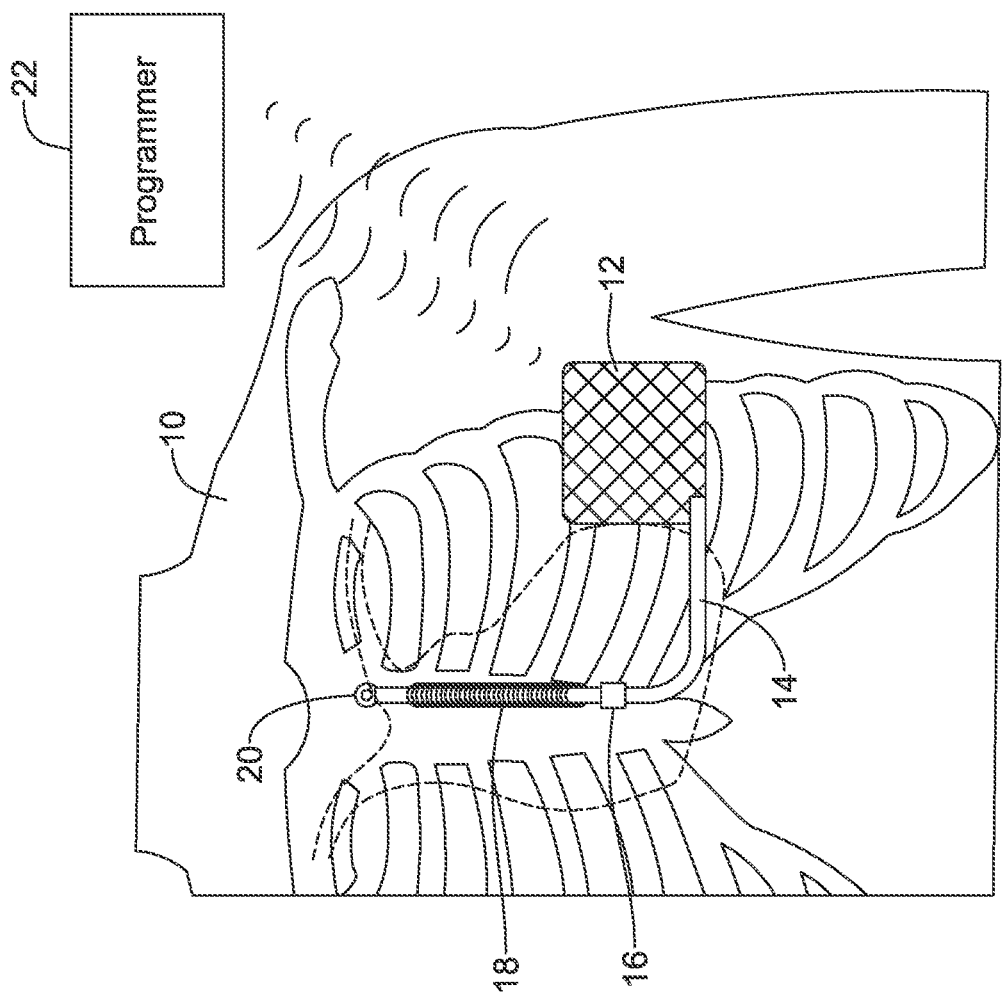
FIG. 1 shows an illustrative subcutaneous-only implantable cardiac stimulus system in an implanted state.
Figure 2:
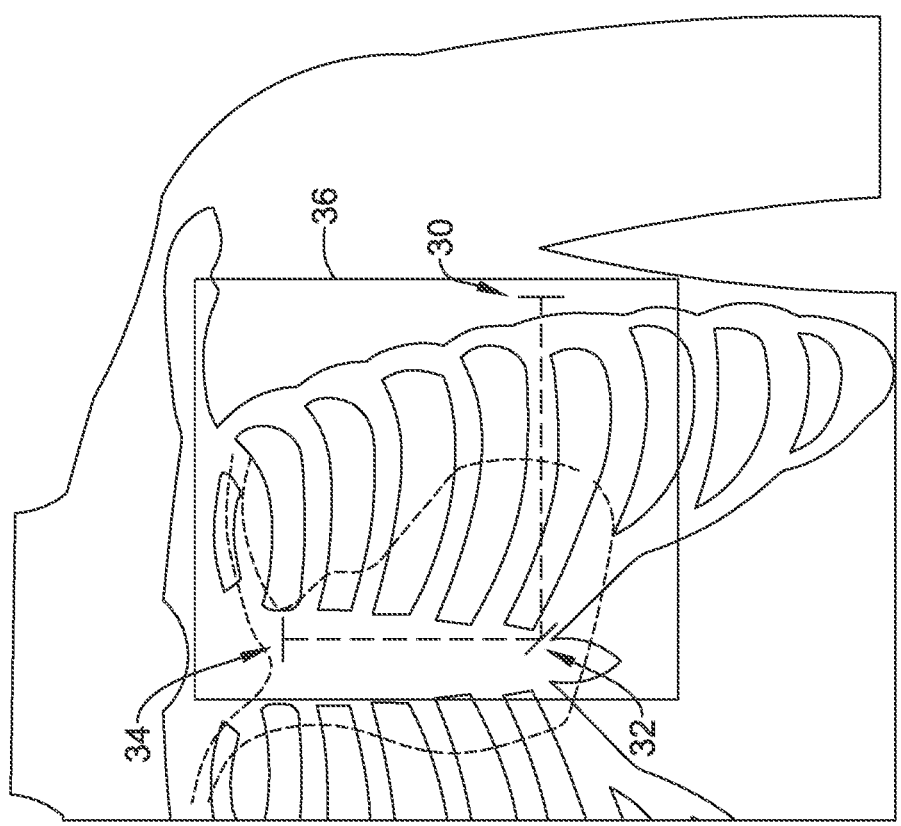
FIG. 2 illustrates certain aspects of the procedure to implant a device as in FIG. 1.
Figure 3:
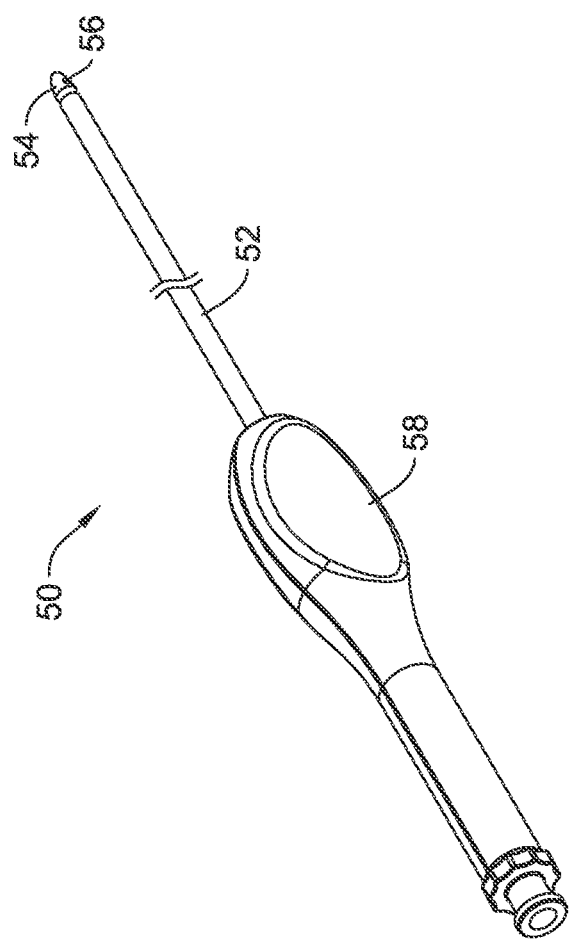
FIG. 3 shows an illustrative lead insertion tool.
Figure 6:
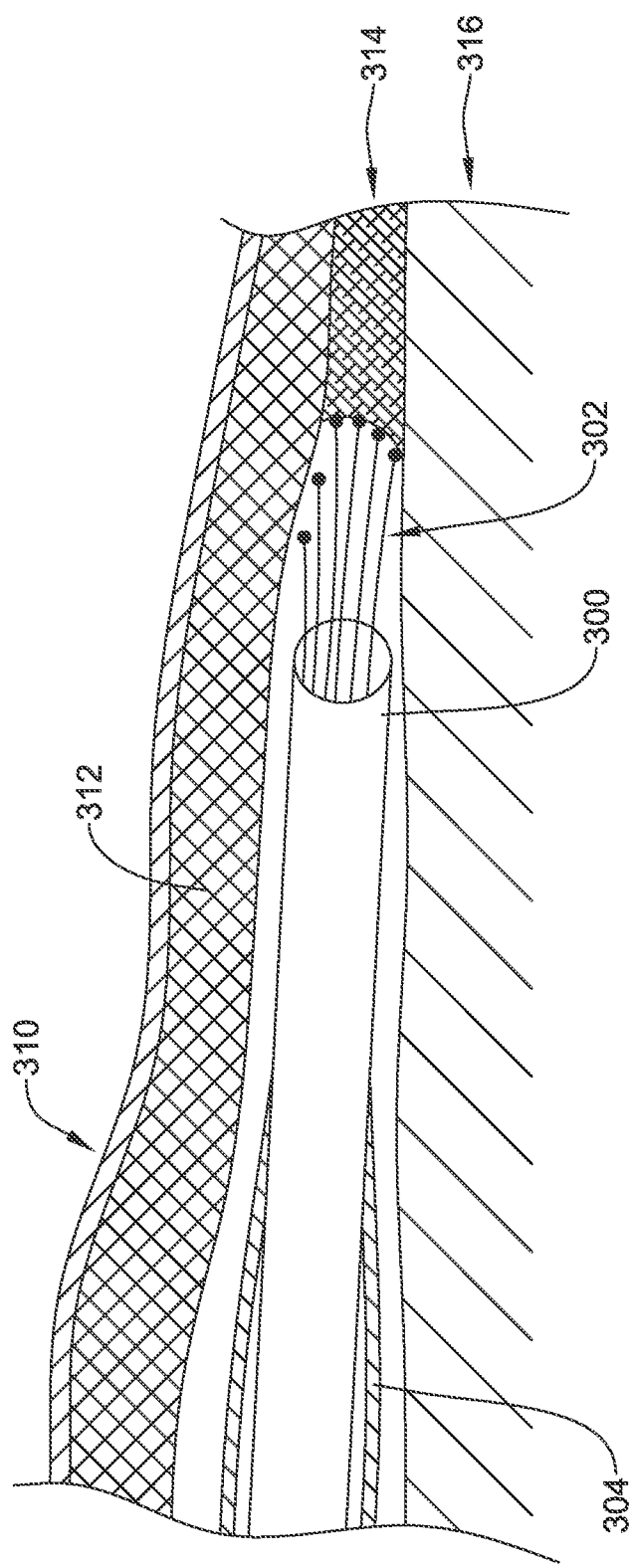
FIG. 6 shows tunneling with an illustrative embodiment.

FIG. 6 shows tunneling with an illustrative embodiment. The dottering tool 300 includes dottering elements 302 having dottering tips and stylets attached thereto. The dottering tool 300 is shown passed through a sheath 304. The reciprocating motion of the dottering elements 302 causes dissection that separates the skin 310 and subcutaneous fat 312 from the underlying muscle layer 316 (which in some locations may instead be the subcutaneous fascia) by tunneling through the loose fat and connective tissue 314. The motion of the dottering elements 302 may allow tunneling through tissue 314 in a smoother and more controlled, and more readily steerable, manner than with a simple blunt tip as shown above in FIG. 3.

Figure 7:
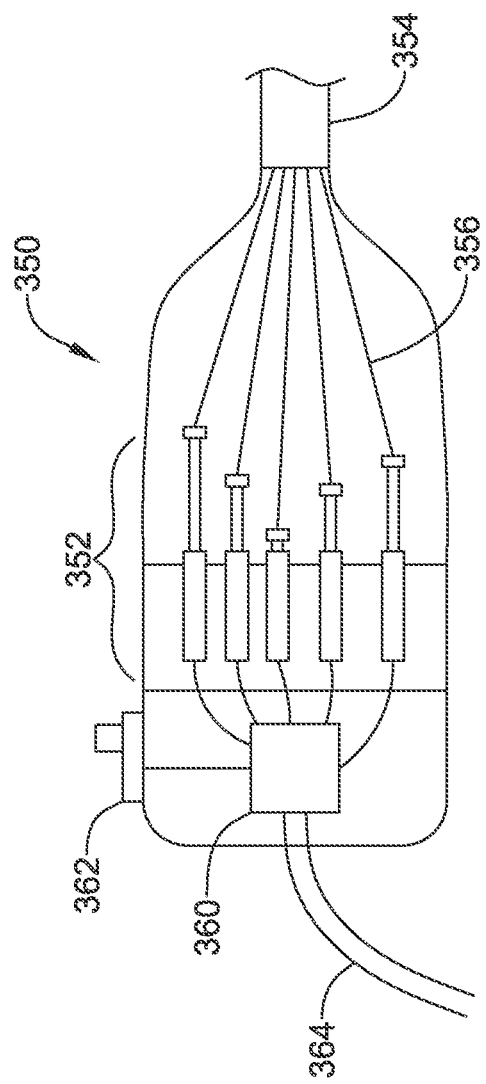
FIG. 7 shows another illustrative embodiment with linear actuators.

FIG. 7 shows another illustrative embodiment with linear actuators. In this example, the device 350 includes an array of individual actuators at 352, each of which is shown as a piston/pump. A catheter 354 is attached to the handle and receives the individual stylets 356 attached to individual actuators 352.

In this example, the actuators 352 can be activated in any desired sequence or combination by control 360. An on/off switch is shown at 362, and connection to a pneumatic source is shown at 364. In other examples, item 364 may connect to a control pedal, or to an electric source. In an alternative example, item 354 may be a directional control element such as that shown in FIG. 5B, above.

In one alternative example, a single actuator 352 may be attached to multiple dottering elements having varying lengths, allowing the dottering action to be achieved from one actuator. In other examples, more than one actuator 352 is provided, with each actuator 352 coupled to subsets or individual ones of the dottering elements via stylets 356.

Figure 8:
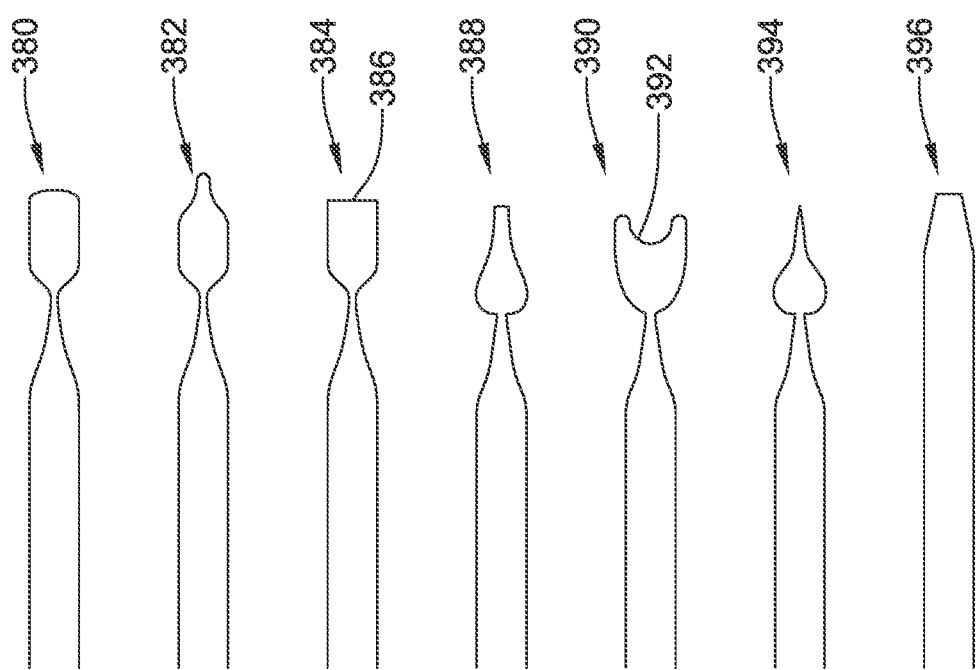
FIG. 8 shows several illustrative dottering tips.

FIG. 8 shows several illustrative dottering tips. In on example, the tip is blunt and rounded as shown at 380. In another example, the tip is pointed, as shown at 382. In another example, the tips are flat on one edge 386 and tapered on the other edge, like a slot head screwdriver, as shown at 384 and 388. In yet another example, the tips are in the shape of a fork, with extending edges as shown at 390 around a recessed portion at 392, with a taper as shown in profile at 394. In still a further example, the tip is simply a blunted taper as shown at 396. The designs shown are merely illustrative, and other designs may be used instead.

The tips may be formed of any suitable material, such as stainless steel, titanium, nickel titanium (Nitinol) or other medical grade material including, for example, various biocompatible polymers. In some examples, the tips are attached to individual stylets by, for example, welding, adhesive, and/or compression fit. In other examples, the tips are formed on the individual stylets by compression, heat and/or grinding.

Multiple different tips may be provided in a single tool. For example, some tips of a first type may be selected for dissecting connective tissue, while others are selected for clearing away tissue as it is dissected. In another example, different groups dottering elements may be actuated separately, based for example on groups having different tip designs (sharp versus blunt, for example), or based on spatial placement at the distal end of the catheter (for example actuating the dottering elements on just one side of the distal tip to steer the distal end during advance the product).

Figure 9:
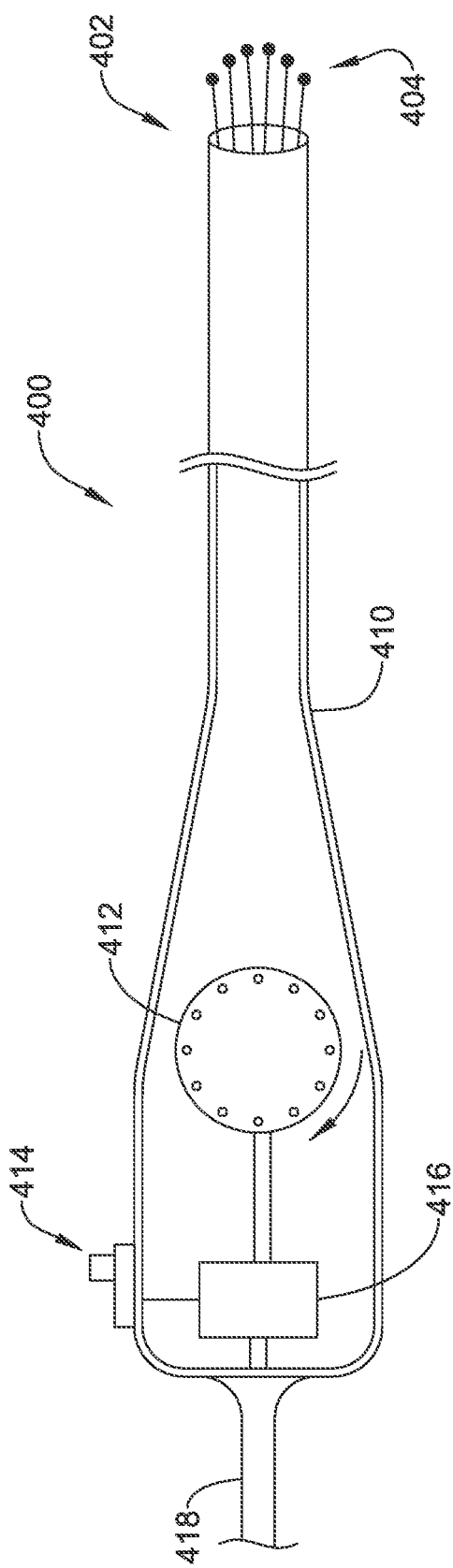
FIG. 9 shows an illustrative externally powered insertion tool.

FIG. 9 shows an illustrative externally powered insertion tool. The overall device 400 includes a distal tip 402 from which dottering elements 404 extend, and a proximal handle 410. In this example, a drive disk 412 is connected to an electric motor 416 having an on/off switch at 414 and a coupling to a control pedal 418. The handle 410 may be shaped in a manner similar to that of the conventional insertion tool shown above in FIG. 3. Power may be supplied with batteries or may be line power.

Figure 10:
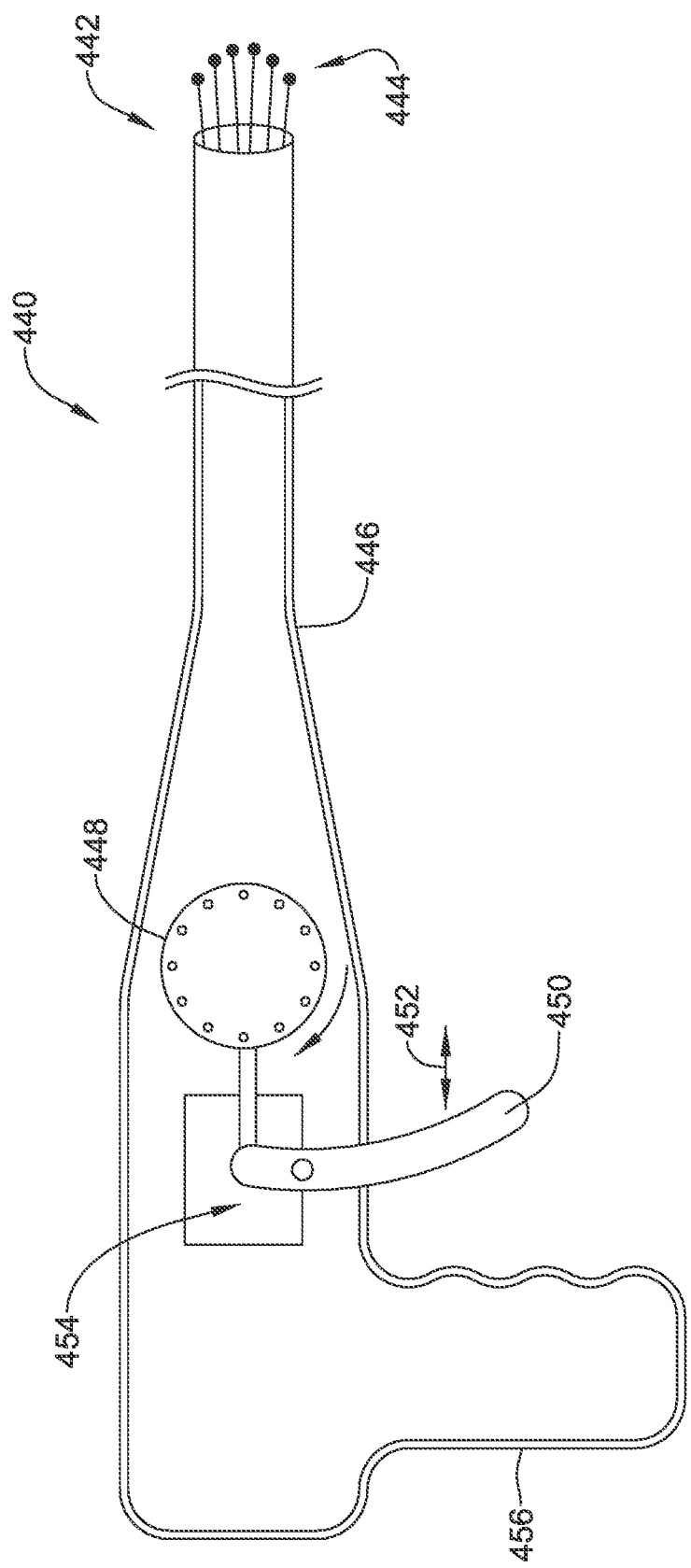
FIG. 10 shows an illustrative manually driven insertion tool.

FIG. 10 shows an illustrative manually driven insertion tool. Here the tool 440 includes a distal tip 442 having dottering elements at 444 and a proximal handle 446. The handle 446 includes a drive disk at 448, which is mechanically coupled to a trigger 450 attached to pivot 454. The trigger may be spring biased to a forward position such that pulling the trigger 450 toward the pistol grip 456, as shown at 452, causes the disk 448 to rotate in one direction, with release of the trigger allowing the spring to relax, as shown at 452, and rotate disk 448 in the opposite direction.

FIG. 11 shows a patient being implanted with a steerable insertion tool and sheath. The patient 500 is undergoing an operation including advancing various items through an incision at 502 toward the xiphoid process. This particular operation is merely illustrative; the tools shown herein may be used in any subcutaneous location, as well as for accessing other bodily locations. For example, other procedures may use a dottering tool as shown herein for other purposes, such as for implants in the heart or blood vessels of the heart, for spinal locations for neurological purposes, for operations in the digestive tract, or any other location such as the biliary tree or kidneys.

In the example of FIG. 11, a dottering tool is shown at 504 having a shaft that extends from a handle 508 to a distal tip that has been inserted to a xiphoid location 510. The dottering tool 504 is shown inserted through an insertion sheath 506 that is inserted through the incision 502. The dottering tool 504 includes steering controls shown illustratively at 512 as, essentially, switches; triggers or other designs may also be used.

In an illustrative example, the insertion sheath 506 is relatively stiff to provide pushability for a proximal portion of the dottering tool 504. As shown at 510, the dottering tool 504 has been manipulated using switches 512 to deflect its distal tip in a desired direction at the location where the insertion sheath 506 has been exited. While making a turn such as that shown at 510, the physician may palpate the device through the skin to aid in guiding the device tip in a desired direction.

Figure 12:
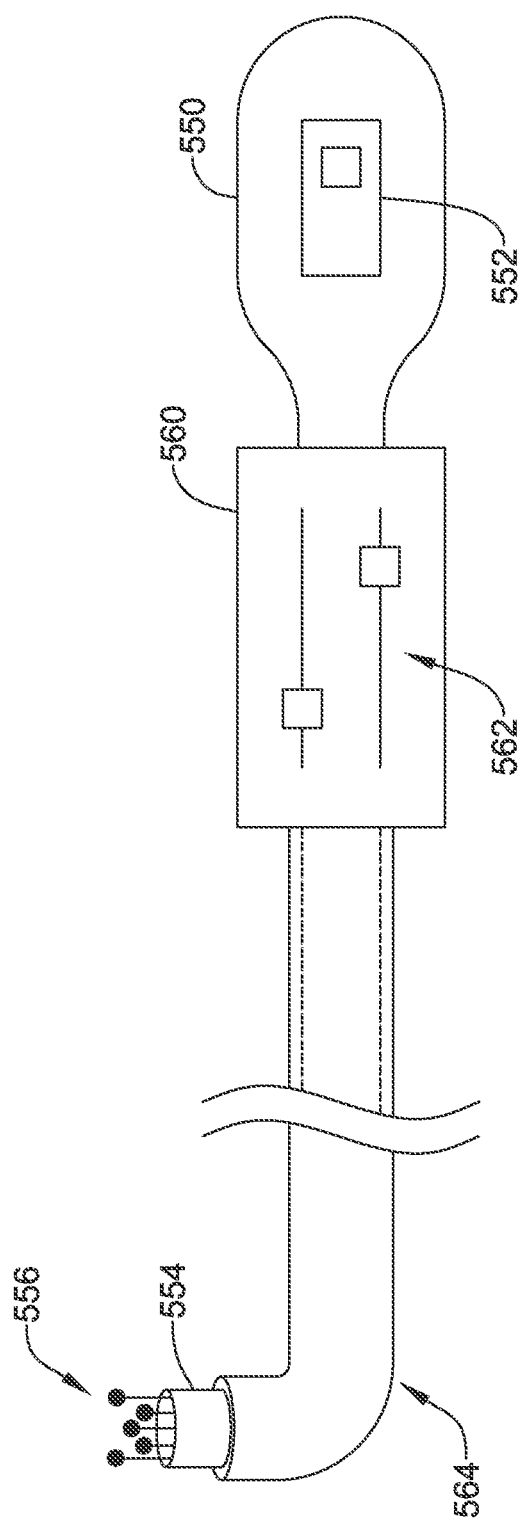
FIG. 12 shows an illustrative insertion tool in a steerable sheath.

FIG. 12 shows an illustrative insertion tool in a steerable sheath. In this example, a dottering tool 550 having an on/off switch at 552 is shown with its distal tip 554 and dottering elements 556 exiting the steerable sheath 560 near the distal end thereof. The sheath is shown with steering control 562 may be coupled to a plurality of control wires that extend through the steerable sheath 560 on different sides thereof to provide steering control. For example, manipulating the steering control 562 will pull a first wire on one side of the sheath 560 to cause a deflection in a first direction. As many pull wires and controls 562 as desired may be provided. In the example shown, the pulling of one of the controls 562 has caused deflection at curve location 564. This turning of the distal end of the sheath 560 directs the dottering tool 550 at its distal end 554 in a desired direction.

Figure 13:
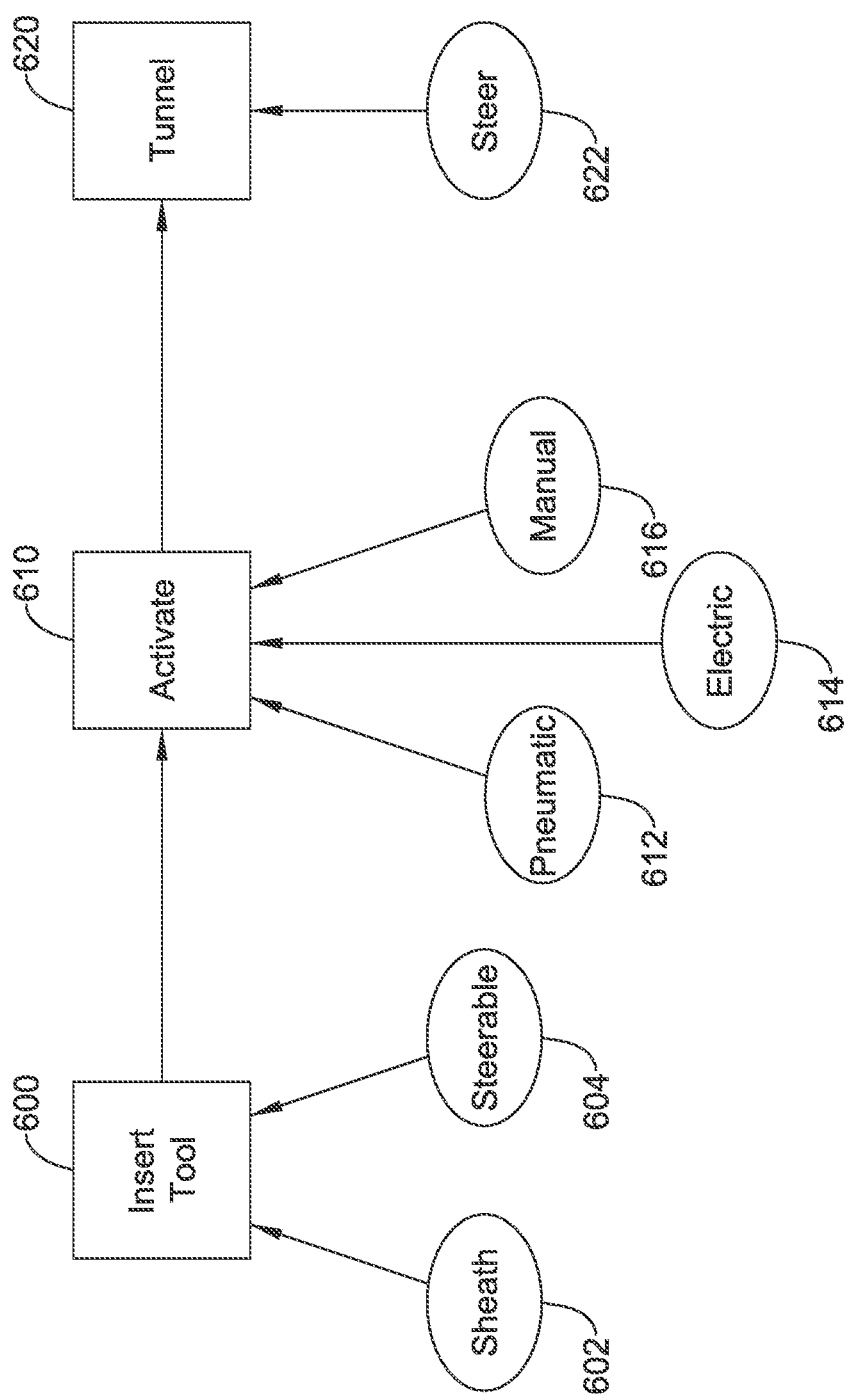
FIG. 13 is a block diagram for an illustrative method.

FIG. 13 is a block diagram for an illustrative method. The method begins by inserting a dottering tool into the patient as shown at 600. Step 600 may include insertion via an incision or existing opening. A sheath may be used, as indicated at 602. One or both of the dottering tool and, if included, sheath, may be steerable as noted at 604.

The method continues with the physician or other user activating the dottering tool 610. Activation may be pneumatic 612, electric 614, or manual 616. Other activation methods may be used instead, as desired, including magnetic or other manners of applying force.

Once activated at 610, the tool is advanced to create a tunnel at 620. Tunneling may be performed with steering control, as noted at 622. In some examples, the tunnel formed is subcutaneous. In other examples, the tunnel may be through a blocked portion of the vasculature, a spinal region, or a portion of the digestive tract.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method of implanting a subcutaneous lead using a dottering tool to establish a tunnel for the subcutaneous lead, the dottering tool having a catheter with proximal and distal ends, a handle at the proximal end of the catheter, a plurality of stylets having dottering tips, and an actuator coupled to the plurality of stylets to drive the stylets in reciprocating motion, the method comprising:

inserting the dottering tool through an incision into a subcutaneous space of a patient;

activating reciprocating motion of the plurality of dottering tips; and forming a tunnel by advancing the dottering tool with the dottering tips activated in reciprocating motion through subcutaneous tissue of the patient, wherein the dottering tips dissect the subcutaneous tissue by their reciprocating motion as the tunnel is formed by advancement of the dottering tool: and wherein the plurality of dottering tips includes at least a first dottering tip and a second dottering tip and the motion of the plurality of dottering tips causes the first dottering tip to reach a position of greatest extension from the catheter at the same time that the second dottering tip is retracted within the catheter.

2. The method of claim 1 further comprising:
   inserting the dottering tool into a steerable sheath; and
   using the steerable sheath to direct the dottering tool along a desired subcutaneous path.

3. The method of claim 1 wherein the dottering tool comprises a steering wire coupled to a steering control at the handle of the dottering tool, such that the catheter is steerable, wherein the step of forming a tunnel by advancing the dottering tool includes using the steering control to direct the distal end of the catheter along a desired subcutaneous path.

4. The method of claim 1 wherein the step of activating reciprocating motion of the plurality of dottering tips includes enabling electrical actuation of the plurality of dottering tips.

5. The method of claim 1 wherein the step of activating reciprocating motion of the plurality of dottering tips includes enabling pneumatic actuation of the plurality of dottering tips.

6. The method of claim 1 wherein the step of tunneling is performed such that the tunnel extends from the left axilla of the patient to about the xiphoid of the patient.

7. The method of claim 6 wherein the step of tunneling includes establishing a curve in a region of the xiphoid of the patient and extending the tunnel cephalic and parallel to the sternum.

* * * * *